(12) United States Patent
Bader

(10) Patent No.: US 9,241,913 B2
(45) Date of Patent: Jan. 26, 2016

(54) POLYSIALIC ACID-BASED N-TRIMETHYL CHITOSAN GEL NANOPARTICLES FOR SYSTEMIC DRUG DELIVERY

(75) Inventor: Rebecca A. Bader, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 560 days.

(21) Appl. No.: 13/474,749

(22) Filed: May 18, 2012

(65) Prior Publication Data
US 2012/0294904 A1    Nov. 22, 2012

Related U.S. Application Data

(60) Provisional application No. 61/487,989, filed on May 19, 2011.

(51) Int. Cl.
*A61K 31/726* (2006.01)
*A61K 9/51* (2006.01)
*A61K 31/519* (2006.01)
*B82Y 30/00* (2011.01)

(52) U.S. Cl.
CPC .............. *A61K 9/5161* (2013.01); *A61K 31/519* (2013.01); *B82Y 30/00* (2013.01)

(58) Field of Classification Search
None
See application file for complete search history.

(56) References Cited

PUBLICATIONS

Doelker et al.; Preparation Techniques and Mechanisms of Formation of Biodegradable Nanoparticles from Preformed Polymers, 1998; Marcel Dekker; Drug Development and Industrial Pharmacy, vol. 24, No. 12, pp. 1113-1128.*
Bader, Rebecca et al.; "Polysialic Acid-Based Micelles for Encapsulation of Hydrophobic drugs," published online Jan. 10, 2011; American Chemical Society, Biomacromolecules, vol. 12, No. 2, pp. 314-320.*
Hejazi, Radi and Amiji, Mansoor; "Polymeric Biomaterials," 2nd ed., 2001, Chapter 10: "Chitosan-Based Delivery Systems: Physicochemical Properties and Pharmaceutical Applications," pp. 1-27, as provided.*
Rao, Panduranga et al.; "pH-Responsive Gelatin Microspheres for Oral Delivery F Anticancer Drug Methotrexate," 1995, John Wiley & Sons; Journal of Applied Polymer Science, vol. 58, pp. 1761-1769.*
Gregoriadis, Gregory et al.; "Improving the therapeutic efficacy of peptides and proteins: A role for polysialic acids," 2005; Elsevier, International Journal of Pharmaceutics, vol. 300, pp. 125-130.*
Sashiwa, Hitoshi et al.; "Chemical Modification of Chitosan: preparation of chitosan-sialic acid branched polysaccharide hydrids," 2000, The Royal Society of Chemistry; Chemical Communications, 2000, pp. 909-910.*
Boddohi, Soheil, et al.; "Polysaccharide-Based Polyelectrolyte Complex Nanoparticles from Chitosan, Heparin, and Hyaluronan," 2009; American Chemical Society, Biomacromolecules, vol. 10, No. 6, pp. 1402-1409.*

* cited by examiner

*Primary Examiner* — Suzanne Ziska
*Assistant Examiner* — Ivan Greene
(74) *Attorney, Agent, or Firm* — David L. Nocilly; George R. McGuire; Bond Schoeneck & King, PLLC

(57) ABSTRACT

Gel nanoparticles for encapsulating and delivering a pharmaceutical compound to a patient. The nanoparticles are formed from N-trimethyl chitosan and polysialic acid, preferably in the presence of sodium tripolyphosphate. A ratio of polysialic acid to N-trimethyl chitosan of about 0.5 to 1 produces nanoparticles having diameter of about 100 nm (plus or minus 25 nm) and a zeta potential above 30 milivolts that can stability contain a pharmaceutical compound, such as methotrexate, for delivery to a patient.

6 Claims, 11 Drawing Sheets

POLYSIALIC ACID-BASED N-TRIMETHYL CHITOSAN GEL NANOPARTICLES FOR SYSTEMIC DRUG DELIVERY

CROSS-REFERENCE TO RELATED APPLICATIONS

The present application claims priority to U.S. Provisional Application No. 61/487,989, filed on May 19, 2011.

STATEMENT REGARDING FEDERALLY SPONSORED RESEARCH OR DEVELOPMENT

This invention was made with government support under grant no. CBET-1032506 awarded by the National Science Foundation. The government has certain rights in the invention.

BACKGROUND OF THE INVENTION

1. Field of the Invention

The present invention relates to poly(sialic acid) nanoparticles for use in drug delivery applications. The invention also relates to methods for treating systemic diseases and neurological disorders using poly(sialic acid) nanoparticles for drug delivery.

2. Description of the Related Art

One century ago, Paul Ehrlich proposed that drugs should be developed to selectively treat diseased cells without damaging healthy tissues. Directed by this concept, many studies have been done to investigate various materials as potential drug delivery systems for a number of diseases with broad goals of facilitating controlled release, improving efficacy, and reducing side effects. Among the different types of drug delivery systems, nanoparticles have drawn the most attention due to numerous benefits, such as reduced toxicity, as well as improved efficacy, bioavailability, and solubility. Furthermore, nanoparticles have been demonstrated to accumulate passively within tumor tissue due to the EPR (enhanced permeability and retention) effect. For systemic drug delivery, one of the most sought after properties is a long circulation time that can increase the chance of accumulation in diseased tissues, which can thereby improve drug efficacy.

Chitosan is a very popular natural polymer for drug delivery because it is non-toxic, biodegradable, biocompatible and bioadhesive. A quaternized derivative of chitosan, N,N,N-trimethyl chitosan (TMC) is soluble and positively charged regardless of pH, as opposed to chitosan that possesses a pHdependent charge. Therefore, TMC has also been widely used. To date, chitosan and its derivatives have been investigated as the basis of nanoparticles by many researchers for the delivery of low molecular weight drugs, DNA, proteins and antigens. With the presence of chitosan and/or its derivatives, a number of the latter therapeutics have shown higher uptake by diseased tissue, less toxicity, and greater specificity.

Despite these advantages, however, the application of chitosan-based nanoparticles is limited by poor stability under physiological conditions, poor efficacy in vivo, and a large size that is unfavorable for systemic drug delivery. Furthermore, due to their cationic nature, chitosan-based nanoparticles are prone to react with negatively charged components in the blood circulation, which can increase the rate of clearance by reticuloendothelial system (RES) and phagocytes. As a result, to date, few nanoparticles based upon chitosan or its derivatives are ideal for systemic drug delivery due to an overly cationic nature, a typically large size, and a propensity to aggregate.

Thus, there is a need in the art to develop nanoparticle carrier systems for drug delivery for the treatment of systemic diseases, such as rheumatoid arthritis (RA), and neuronal disorders, such as spinal cord injury (SCI) that employ a material for which the body possesses no known receptors to prevent premature clearance of the drug delivery carrier system. In addition, for drug delivery, the nanoparticles must be of proper size and charge to achieve high efficacy and low toxicity of associated therapeutics.

For example, rheumatoid arthritis is a chronic autoimmune disease characterized by inflammation of the synovial membrane that lines the non-weight bearing surface of joints. In the normal anatomy this layer provides lubrication and nourishment to the joints through the action of synovial fluid. In RA, however, this tissue becomes enlarged and inflamed eventually invading and destroying articular cartilage and bone. This condition typically begins to affect the small diarthrodal joints of the hands and feet and spreads symmetrically throughout the joints of the body to become a polyarticular arthritis. As such, rheumatoid arthritis leads to irreversible joint damage, disability, and deformity. In addition to this, those individuals diagnosed with this autoimmune condition often experience extra-articular organ involvement and, in particular, have an increased risk of ischemic heart disease and a decreased life expectancy.

Rheumatoid arthritis has been traced back several thousand years to Native American tribes in North America and is evident in European paintings that date back to the 1600s. As of 2003, RA was the most common of the more than one hundred rheumatic diseases known and currently 0.5% to 1% of the adult population worldwide suffers from this condition. Women in particular are more likely to acquire rheumatoid arthritis and there continues to be a much larger occurrence of this disease in the descendants of Native American tribes with a prevalence of up to 5%. Due to the high emotional, physical, and financial burdens this condition presents, researchers have been motivated to expend great effort in understanding the pathogenesis of rheumatoid arthritis in order to develop safer and more effective treatments. While progress has been made in understanding the complex process behind the pathogenesis of rheumatoid arthritis, the precise pathophysiological causes of RA remain largely a mystery, and therefore treatment methods have not been optimized.

Methotrexate (MTX) was originally developed in the 1950s as a cancer therapy and gained popularity as a disease modifying anti-rheumatic drug (DMARD) in the 1970s. DMARDs are able to treat rheumatoid arthritis by reducing immune function, but many are cytotoxic. Today, methotrexate is the most commonly used DMARD and in randomized controlled trials has been found to be equal or superior to all other DMARDs. In fact, for more than twenty years, the European League Against Rheumatism and the American College of Rheumatology have recommended methotrexate as a first line treatment for rheumatoid arthritis. In addition, a 60% reduction in the risk of early mortality in RA patients treated with methotrexate has been observed, as well as a 70% reduction in deaths due to RA related cardiovascular disease in individuals prescribed methotrexate.

In terms of chemical properties, methotrexate is an antimetabolite that interferes with the metabolism of folic acid, which is necessary for cell growth, and has been shown to control both symptoms and disease activity. Methotrexate enters cells through either the reduced folate carrier or folate receptor f3, which is overexpressed in rheumatoid arthritis synovial macrophages. While the mechanism of methotrexate action in the treatment of rheumatoid arthritis is uncertain, it appears to reduce the proliferation of infiltrating inflammatory cells and/or suppresses the release of pro-inflammatory cytokines.

In spite of methotrexate being the gold standard of treatment for rheumatoid arthritis, a major constraint on its use and effectiveness is the occurrence of adverse side effects. Methotrexate has been linked to several adverse reactions often associated with antimetabolites, such as cytopenia, hypersensitivity pneumonitis, bone-marrow suppression, gastrointestinal issues, and liver damage. The most common adverse effects of methotrexate are gastrointestinal problems and liver damage. Due to the hepatotoxic nature of methotrexate, patients receive periodic liver function tests and biopsies. In spite of these precautionary measures, however, cirrhosis and liver fibrosis continue to be negative consequences of methotrexate use. In fact, 3% of patients prescribed methotrexate for the treatment of rheumatoid arthritis developed severe fibrosis or cirrhosis over 55 months of treatment with methotrexate. These side effects are of greater risk in those individuals who drink at least one hundred grams of alcohol per week. All side effects of methotrexate are concerning as both potentially life-threatening and more minor side effects may lead to termination of treatment, even if therapeutic efficacy is satisfactory.

In addition to the risk of serious side effects associated with methotrexate, this drug also presents an unfavorable pharmacokinetic profile. The bioavailability and peak serum concentration of orally administered methotrexate varies between patients and elimination half-lives are inconsistent, ranging from six to fifty-five hours. The large variability in the pharmacokinetics of methotrexate likely contributes to its toxicity in some patients. Due to the high occurrence of adverse side effects and variability in drug effectiveness, the development of a method for the delivery of methotrexate in such a way as to specifically target the pannus tissue and reduce extra-organ toxicity would be a significant progression in the treatment of rheumatoid arthritis.

BRIEF SUMMARY OF THE INVENTION

It is therefore a principal object and advantage of the present invention to provide a nanoparticle carrier system for which the body posses no known receptors.

It is an additional object and advantage of the present invention to provide a nanoparticle carrier system that can be used to more safely and effectively deliver drugs for the treatment of autoimmune diseases.

It is a further object and advantage of the present invention to provide a nanoparticle carrier system for the delivery of methotrexate in patients diagnosed with rheumatoid arthritis.

In accordance with the foregoing objects and advantages, the present invention comprises a nanoparticle system comprising poly(sialic acid) (PSA) and N,N,N-trimethylchitosan (TMC). The PSA-TMC nanoparticles are synthesized by complexing positively charged TMC with negatively charged PSA. At a weight ratio of 0.5 PSA:1 TMC, the resultant nanoparticles possessed a favorable size of about 100 nm (i.e., plus or minus 25 nm) and a favorable zeta potential (above about 30 mV), and are thus promising for use as a drug delivery system. To further demonstrate the capacity of the nanoparticles to be used in drug delivery, nanoparticles according to the present invention were evaluated for the encapsulation and controlled release of methotrexate (MTX), a therapeutic used in the treatment of both rheumatoid arthritis and cancer, for encapsulation and controlled release. Cytotoxicity and uptake of the nanoparticles was evaluated using a rheumatoid arthritis synovial fibroblast cell line (MH7A).

The present invention also encompasses a method for synthesizing a poly(sialic acid)-based nanoparticle having the appropriate size and stability for use as a therapeutic deliver agent. In one embodiment according to the present invention, the method comprises the step of ionically complexing cationic N-trimethyl chitosan (TMC) with sodium tripolyphosphate (TPP) in the presence of poly(sialic acid) (PSA) to produce nanoparticles having a 0.5:1 ratio of PSA to TMC, thereby resulting in nanoparticles of about 100 nm in size and having a zeta potential of more than 30 mV.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
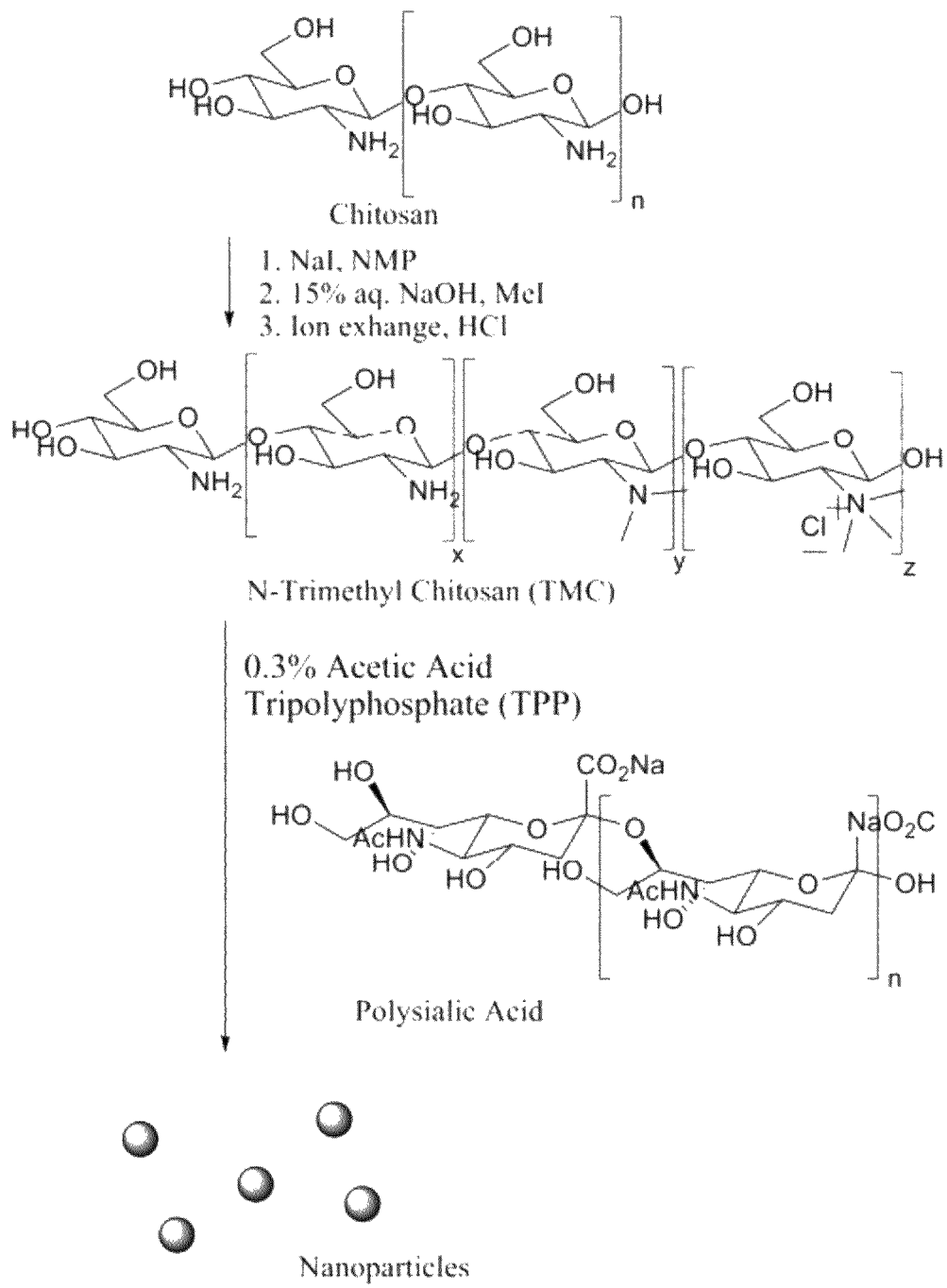
FIG. 1 is a schematic of the synthesis of N-trimethyl chitosan (TMC) and complexation with polysialic acid (PSA) in the presence of tripolyphosphate (TPP) to yield nanoparticles according to the present invention.

Referring now to the drawings, wherein like reference numerals refer to like parts throughout, there is seen in FIG. 1, a poly(sialic acid) (PSA)-based nanoparticle for use in delivery of a therapeutic compound. More specifically, PSA-based nanoparticle were developed via ionic gelation of two polysaccharide-based molecules, negatively charged polysialic acid (PSA) and positively charged N,N,N-trimethylchitosan (TMC). PSA is unique in that the highly hydrated backbone may be used in a manner similar to that of poly (ethylene glycol) to extend circulation times. Although not necessary for nanoparticle formation, sodium tripolyphosphate (TPP) was added to enhance stability, as indicated by a reduced polydispersity. Although the present invention was evaluated in three different ratios by weight of PSA:TMC (0.5:1, 1:1, 1:2) and five different TPP concentrations ranging 0.1-0.8 mg/ml, optimal size and surface charge were achieved with a PSA:TMC weight ratio of 0.5:1 and a TPP concentration 0.2 mg/ml. The optimal nanoparticles are characterized by nanoparticles having distinct solid, spherical nano-gels with a size of 106±25 nm, an ideal size to reduce uptake by the reticuloendothelial system while facilitating passive targeting of diseased tissue. The zeta potential of the nanoparticles was +33.9±1.2 mV, suggesting that the nanoparticles will be stable under physiological conditions. Encapsulation and controlled release by the nanoparticles was demonstrated using methotrexate, a therapeutic indicated in both cancer and rheumatoid arthritis.

EXAMPLE 1

TMC synthesis, as well as ionic complexation with TPP to form nanoparticles, may also be seen in FIG. 1. TMC was synthesized according to a one-step method, previously described bed by Sieval et al. A. B. Sieval et al., Carbohydr. Polym. 36, 157 (1998), hereby incorporated by reference. As an example, 0.5 g (0.0031 mol) chitosan and 1.2 g (0.008 mol) sodium iodide were added into 20 ml anhydrous N-methyl pyrrolidinone in a nitrogen purged 3-neck flask. The solution was reacted at 60° C. for 1.5 hrs with a stifling speed of 190 rpm. Then, 4.13 ml 1 M NaOH (0.0041 mol NaOH) and 2.88 ml (0.046 mol) methyl iodide were added and stirring was continued for another 1 hr at 60° C. The reaction solution was then added dropwise to cold ethanol. The yellow precipitate was collected by vacuum filtration. For further purification, the product was dissolved in 15 ml DI water and precipitated again in 62 ml of 1M HCL in ethanol. 0.626 g of white, solid product was obtained after vacuum filtration and evaporation overnight in a vacuum oven. The degree of quaternization (DQ) of TMC was determined by 1H-NMR (Bruker DPX-300) in D2O. The DQ was calculated by the following equation:

DQ (%)=[($\int TM$/$\int H$)×1/9]×100, where $\int TM$ is the integral of 1H trimethy amino group peak at 3.0-3.2 ppm and $\int H$ is the integral of 1H peak from C1 of the glycoside ring from 4.9 ppm to 5.5 ppm.

Ten sets of PSA-TMC nanoparticles were prepared by varying the ratio of PSA:TMC or the TPP concentration (see Table 1 below). The method was similar to those previously established in the art for ionic gelation of chitosan/TMC with TPP. As an example procedure, to prepare PSA:TMC (0.5:1) with a TPP concentration of 0.2 mg/ml (Group 3, Table TTP concentration of 0.2 mg/ml (Group 3, Table 1)6.4 mg of TMC were dissolved in 3 ml of 0.3% acetic acid in a glass vial. In a separate glass vial, 3.2 mg PSA and 1 mg TPP were mixed well with 2 ml deionized (DI) water. The PSA solution was added drop by drop to the TMC solution while stirring. The solution was stirred for 30 min to stabilize the nanoparticle system. A pellet of nanoparticles was obtained after centrifugation at 3000 rpm for 15 min. Excess supernatant was removed.

TABLE 1

Different weight ratios of PSA:TMC and TPP concentrations used in the preparation of nanoparticles.

| Group | PSA (mg) | TMC (mg) | 0.30% Acetic Acid (ml) | DI Water (ml) | TPP (mg) |
|---|---|---|---|---|---|
| 1 | 0 | 6.4 (Chitosan) | 3 | 2 | 1 |
| 2 | 0 | 6.4 | 3 | 2 | 1 |
| 3 | 3.2 | 6.4 | 3 | 2 | 1 |
| 4 | 6.4 | 6.4 | 3 | 2 | 1 |
| 5 | 12.8 | 6.4 | 3 | 2 | 1 |
| 6 | 3.2 | 6.4 | 3 | 2 | 0 |
| 7 | 3.2 | 6.4 | 3 | 2 | 0.5 |
| 8 | 3.2 | 6.4 | 3 | 2 | 1.5 |
| 9 | 3.2 | 6.4 | 3 | 2 | 2 |
| 10 | 3.2 | 6.4 | 3 | 2 | 4 |

MTX was encapsulated within PSA-TMC nanoparticles (0.5 PSA:1 TMC, 0.2 mg/ml TPP) at a 25% by weight loading percentage. 2.4 mg of MTX were added to the PSA solution, as described above. The PSA solution with MTX was added drop by drop to the stirring TMC solution to yield MTX loaded nanoparticles. Again, the final solution was stirred for 30 min to stabilize the nanoparticle system. MTX loaded nanoparticles were isolated by centrifuging at 3000 rpm for 15 min. 1 ml supernatant was kept following centrifugation to assess loading capacity, as described below, while the remaining supernatant was discarded.

The size and zeta potential of the PSA-TMC nanoparticles were measured using a Malvern Zetasize NanoZS90 (Malvern Instruments Ltd., Malvern, UK). The particle size distribution of the nanoparticles was reported as a polydispersity index (PDI). The nanoparticles were dissolved in DI water at 2 mg/ml and used without filtration. Then, the nanoparticle solutions were transferred to disposable microcuvettes (Malvern Instruments Ltd., Malvern, UK) for size measurements and disposable capillary cells (Malvern Instruments Ltd., Malvern, UK) for zeta potential measurements. For dynamic light scattering measurements, the temperature was set 25° C., and the scattered light was detected at an angle of 173°. All measurements were performed in triplicate.

Morphological examination of the nanoparticles was performed by atomic force microscopy (AFM). A drop of aqueous nanoparticle solution (2 mg/ml) was placed on a thin round glass cover slip that was dried in a desiccator overnight. Images were obtained with a Nanoscope III atomic force microscope (Veeco Instruments Inc., Plainview, N.Y.) in contact mode.

Release studies were performed on the MTX loaded PSA-TMC nanoparticles. Immediately after preparation, nanoparticle solutions were transferred to 15 ml centrifuge tubes and centrifuged at 3000 rpm for 15 mi in 1 ml of supernatant was saved for the loading capacity and efficiency analysis. To begin the release experiments, the nanoparticles were resuspended in 5 ml of DI water, and the nanoparticle solutions were transferred to Spectra/Por (Spectrum Laboratories, Rancho Dominguez, Calif., USA) dialysis tubes (MWCO 12,000-14,000). Dialysis was performed against 45 ml DI water pH 7.4, at 37° C. under static conditions. 1 ml of external medium was withdrawn and immediately replaced with fresh DI water at the following time points: 10 min, 20 min, 40 min, 1 hr, 2 hr, 4 hr, 6 hr, 12 hr, 24 hr, and 48 hr. The release samples were analyzed with a Prominence Ultrafast Liquid Chromatography System (UFLC, Shimadzu Scientific Instruments, Japan) equipped with an SPD-20AV UV detector, an SIL-20A autosampler, an DGU-20A3 degasser, and a Shim-pack XR-ODS/C8/ Phenyl column. The mobile phase was a 93:7 mixture (v/v) of 50 mM aqueous ammonium acetate and acetonitrile that was pumped at a flow rate of 0.5 ml/min. An injection volume of 100 µL was used, and the detection wavelength was set to 210 nm. A calibration curve was constructed by determining the area under the peak of eight MTX solutions with known concentrations ranging from 0.39 µg/ml to 50 µg/ml using PeakFit 4.2 software. Loading capacity (LC) and loading efficiency (LE) were determined using the following equations:

$$LE = \frac{m_{MTX,loaded}}{m_{MTX,added}} \times 100 \quad (1)$$

$$LC = \frac{m_{MTX,loaded}}{m_{nanoparticle}} \quad (2)$$

where $m_{MTX,added}$ is the mass of MTX added to the PSA solution, $m_{MTX,loaded}$ is the mass of MTX loaded into the nanoparticles, and $m_{nanoparticle}$ is the mass of the nanoparticles used for the release study.

WST-8 assay (Cayman Chemical Company, Ann Arbor, Mich.) was conducted on the MH7A rheumatoid arthritis synovial fibroblast cell line, following the manufacturer's instructions, to assess the cytotoxicity of the PSA-TMC nanoparticles. NADH produced within the mitochondria reduces WST-8 tetrazolium salt to formazan dye, which can be quantified by absorbance measurements at 450 nm. Cells were seeded into 96-well cell culture plate (2×104 cells per well) and cultured for 24 hr at 37° C., 5% CO2. PSA-TMC (0.5:1) was added to yield a series of concentrations from 0.3125 to ~20 mg/mL, and the cultures were incubated for an additional 24 hours. 10 µL of WST-8 solution were added to each well. After a 90 minute incubation period, absorbance was measured with a Synergy 2 multimode microplate reader (BioTek Instruments, Winooski, Vt.) at 450 nm. The cytotoxicities of TMC TPP and alone were also evaluated following the above procedure. Untreated MH7A synovial fibroblast cultures were used as controls. Relative absorbance versus concentration was plotted for each set of additives, and a four parameter logistic, constructed with Kaleidagraph software, was used to fit the data to determine the IC50 values. Each experiment was repeated independently at least two times.

Uptake of the PSA-TMC nanoparticles by the MH7A cells was verified with inverted fluorescence microscopy. The MH7A cell s were added to lysine coated Lab-Tek Chamber Slides, and fluorescently tagged nanoparticles (Alexa Fluor 610, Invitrogen) were added 24 hours after seeding. After a short incubation period (about 45 minutes), the nanoparticle solution was removed, the cells were washed with PBS, and uptake was observed with a Nikon Eclipse Ti inverted microscope.

Figures 2A, 2B, 2C:
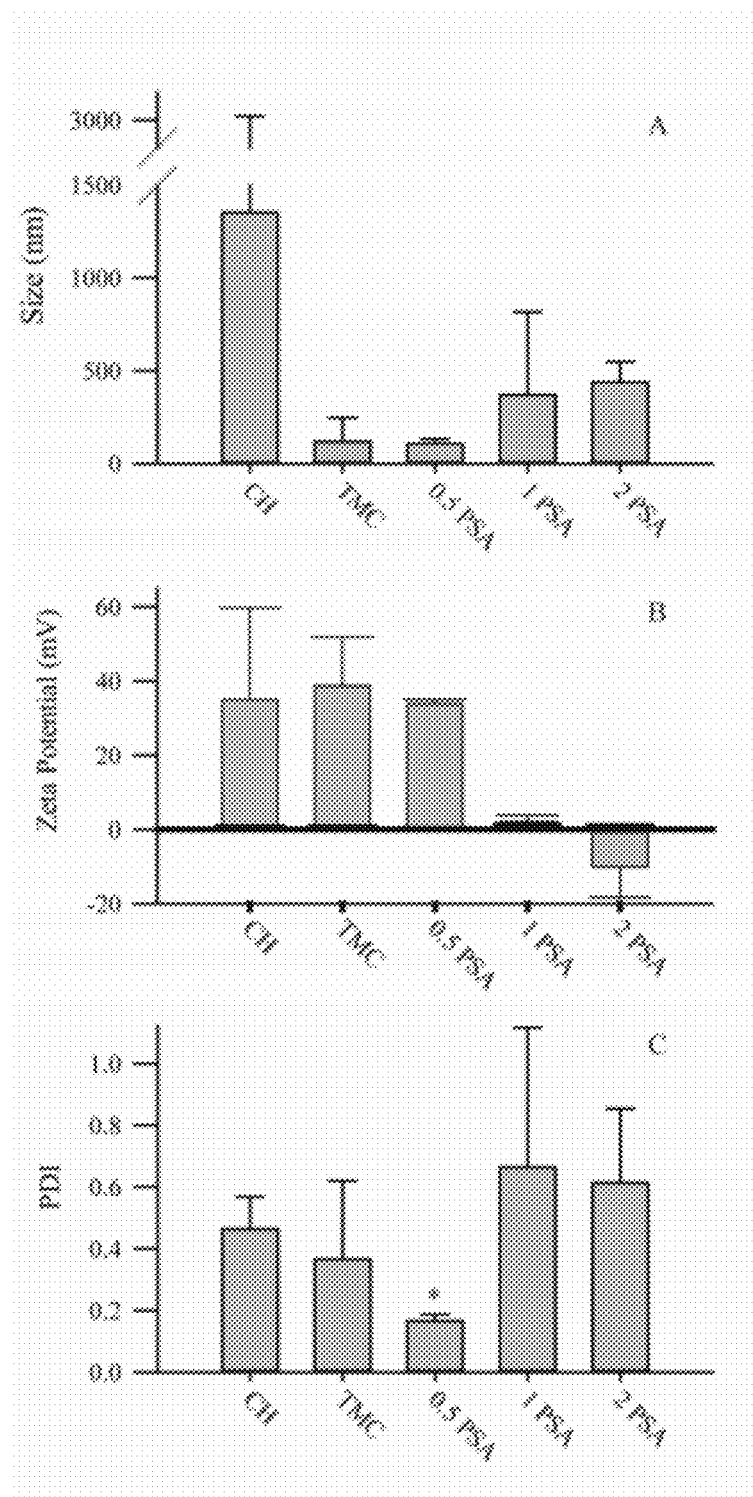
FIG. 2A through 2C are a series of bar charts depicting nanoparticle: (A) size; (B) zeta potential; and (C) PDI as a function of the weight ratio of PSA:TMC, where *$p<0.05$ relative to CH, 1 PSA:1 TMC, and 2 PSA:1 TMC.

Referring to FIG. 2A through 2C, all data supporting the present invention are presented as mean plus or minus standard deviation (N=3). One-way ANOVA and Fisher's LSD post hoc tests were used to test for significant differences (p<0.05).

From the 1H-NM R spectra, a DQ of ~50% was reproducibly obtained. The DQ determines the amount of positive charge in chitosan chains. This consequently has a significant impact on the surface charge of the nanoparticles, which indirectly relates to the size distribution of the nanoparticles due to aggregation. Therefore, to produce TMC with a reproducible DQ of 50% is critical in obtaining reproducible nanoparticles with consistent size distribution.

For the present invention, three different weight ratios of PSA:TMC were investigated, all prepared with TPP concentration of 0.2 mg/ml. Chitosan and 50% modified TMC, with no PSA, were used as controls. The results are summarized in FIG. 2. As indicated by zeta potential values much less than an absolute value of 30, PSA:TMC nanoparticles with weight ratios of 1:1 and 1:2 were not stable. Low zeta potential values are associated with a deficiency of electronic force necessary to keep the nanoparticles separated from each other. Chitosan itself did form particles; however, the size was not favorable for drug delivery. Furthermore, the size variation and size distribution were high, suggestive of a lack of stability and a propensity to aggregate. Presumably, the variability in size with a high PDI was a result of the pH-dependent positive charge. In contrast, pH-independent TMC formed nanoparticles with the desired size; however, the size distribution remained high. In addition, the lack of a hydrophilic component, such as PSA, may result in undesirable uptake by the RES during circulation. A PSA:TMC ratio of 0.5:1 was identified as the only ratio that gave rise to nanoparticles with favorable size, a size distribution that was significantly lower than other formulations, and an appropriate surface charge for systemic drug delivery.

Figures 3A, 3B, 3C:
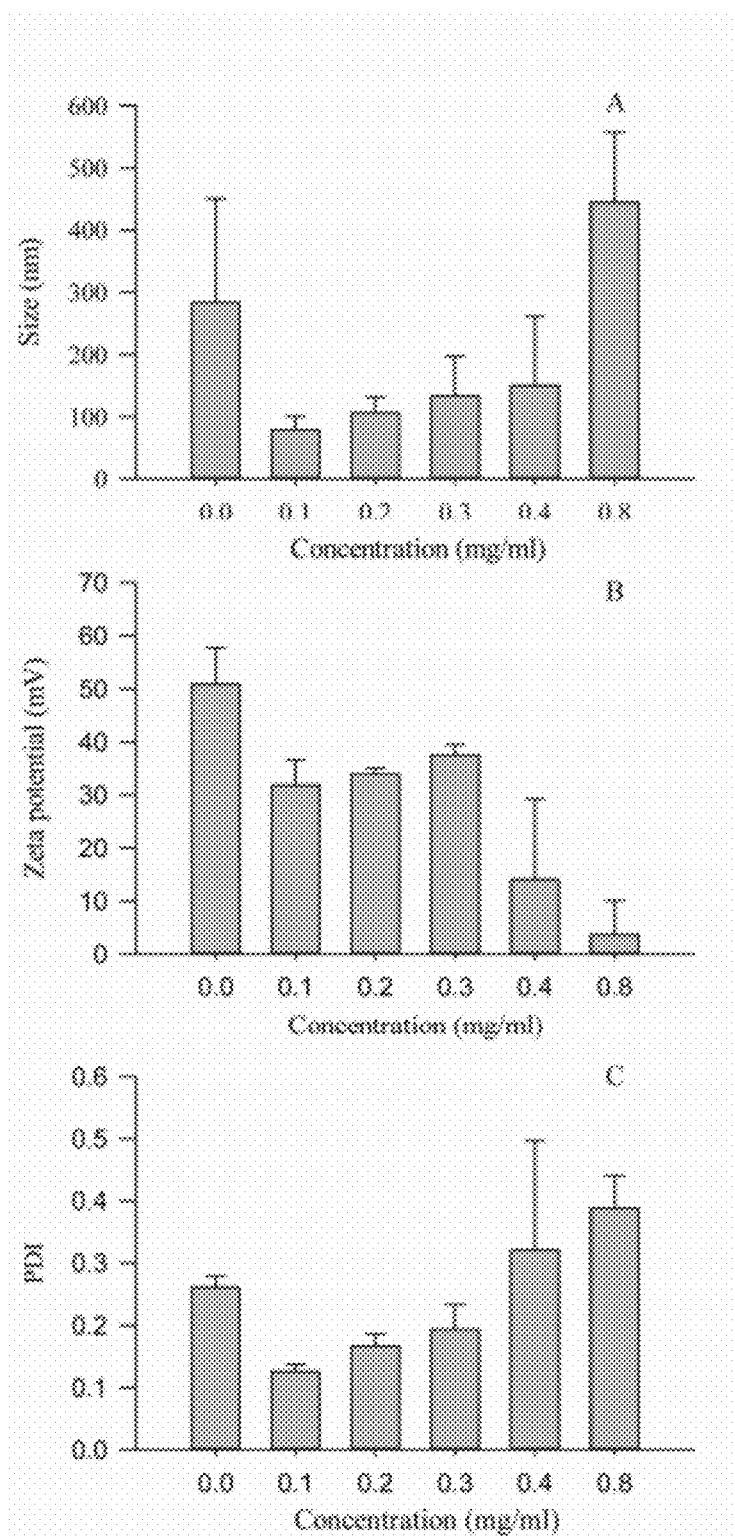
FIG. 3A through 3C are a series of bar charts depicting nanoparticle: (A) size, (B) zeta potential; and (C) PDI as a function of TPP concentration.
Figure 4:
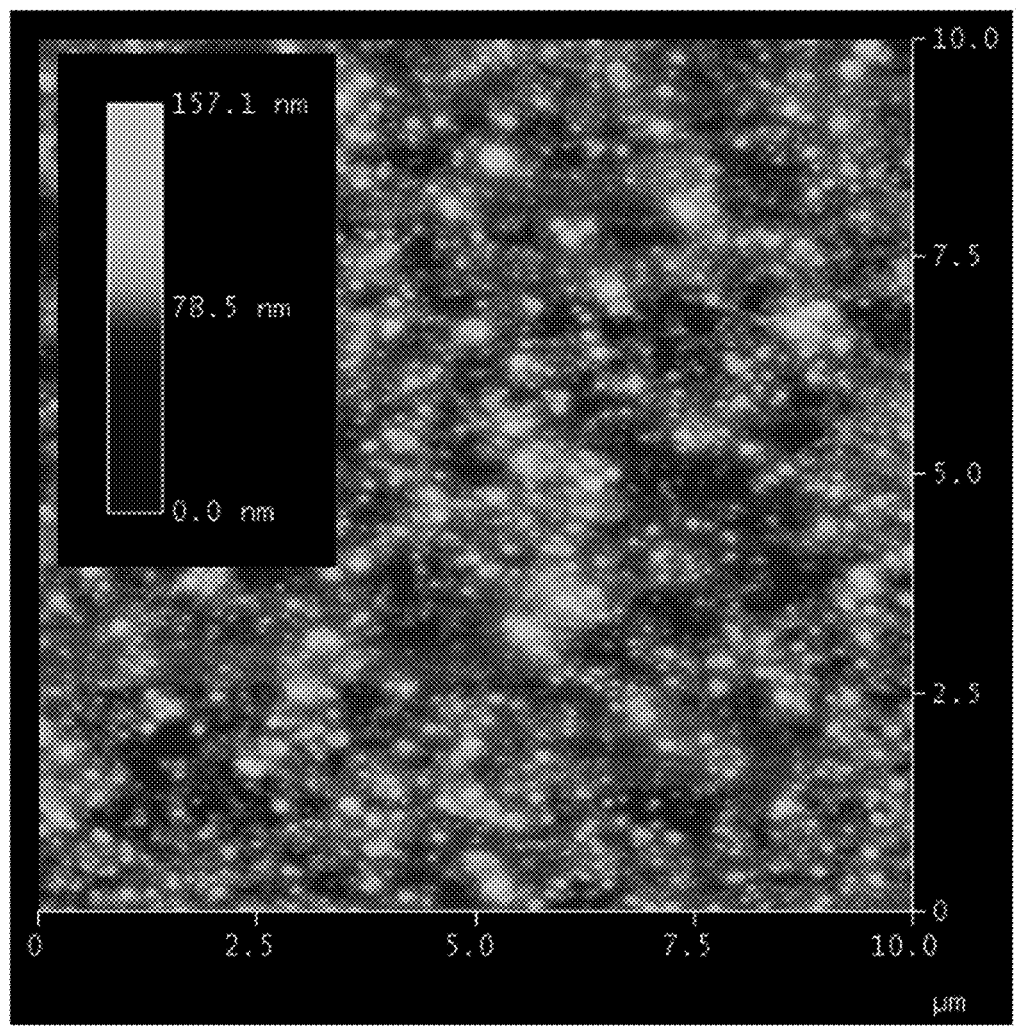
FIG. 4 is an AFM image of PSA-TMC nanoparticles (0.5 PSA:1 TMC, 0.2 mg/ml TPP)
Figure 5:
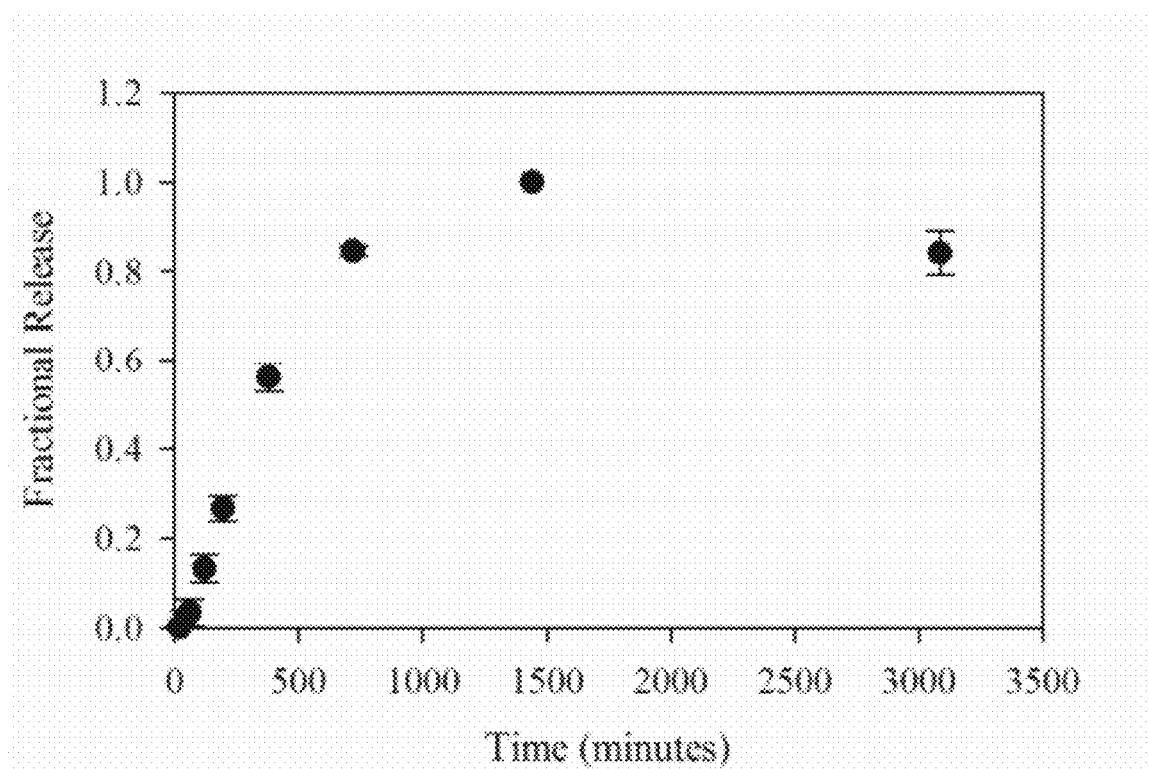
FIG. 5 is a graph showing the fractional release of methotrexate from PSA-TMC nanoparticles according to the present invention (0.5 PSA: 1 TMC, 0.2 mg/ml TPP) as a function of time.

Referring to FIG. 3, five different TPP concentrations were investigated to investigate the effect of TPP concentration on the size distribution of the nanoparticles. Nanoparticles prepared with no TPP were used as controls. At 0.1 mg/ml and 0.2 mg/ml TPP, the resultant nanoparticles were of an appropriate size with a narrow size distribution. As TPP concentration increased, the size of the resultant nanoparticles and size distribution became larger; however, the differences between nanoparticles prepared with 0.1, 0.2, 0.3, and 0.4 mg/ml were not significant. As shown by the zeta potential values, an increasing amount of TPP increased the negative charge of the nanoparticles, thereby neutralizing the positive charge of the TMC. This reduction in nanoparticle surface charge can in turn be linked to an increase in the interaction between the nanoparticles, resulting in particles with larger sizes and size distributions. PSA complexed with TMC in the absence of TPP yielded nanoparticles of the appropriate size; however the PDI was significantly larger than those prepared with 0.1 and 0.2 mg/ml TPP. Based upon these results, a 0.5:1 ratio of PSA:TMC with a TPP concentration of 0.2 mg/ml was identified as the ideal formulation for the formation of stable nanoparticles. As seen in FIG. 4, a small size, with narrow distribution, and a spherical morphology were confirmed by AFM.

MTX was successfully encapsulated into the PSA-TMC nanoparticles with a loading efficiency and loading capacity of 46.3±13.0% and 0.10±0.03 mg MTX/mg nanoparticle, respectively. Dynamic light scattering was used an additional indicator to verify MTX encapsulation. Although the difference was not significant, the MTX loaded nanoparticles were slightly larger than the unloaded nanoparticles (128.7±5.3 vs. 106.3±25.4).

Fractional release of MTX as a function of time from the PSA-TMC nanoparticles may be seen FIG. 3. Although controlled release was observed, the data could not be fit to a simple diffusion controlled model, where the fractional release is proportional to the square root of time. Consistent with other hydrophobic drugs encapsulated into nanoparticles at high loading capacity (≥0.30), the release is presumably dissolution-controlled. An in depth analysis on the mechanism and kinetics of release could be the topic of future studies and assist with understanding the scientific principles at work, but is not necessary for the practice of the present invention.

For applications in diseases, such as rheumatoid arthritis, where the primary goal is not cell death, the cytotoxicity of the nanoparticles must be minimal. As shown in Table 2 below, TMC has some cytotoxicity likely because of the impact of chitosan quaternization on biocompatibility. PSA is not cytotoxic, and incorporation of TMC into nanoparticles with PSA resulted in significantly higher IC50 values than TMC alone. The TMC is ideally released from the nanoparticle at a slow rate that will yield only negligible levels of this potentially harmful polymer when administered in vivo. Somewhat surprising was the extremely low IC50 value observed for TPP given the prevalent use of TPP in forming chitosan TMC nanoparticles.

TABLE 2

IC50 values for TMC, TPP, and PSA-TMC nanoparticles.

|  | $IC_{50}$ (mg/ml) |
|---|---|
| TMC | 2.30 ± 0.84 |
| TPP | 0.22 ± 0.04 |
| Nanoparticles (0.5 PSA:1 TMC) | 7.65 ± 0.07 |

Figure 6:
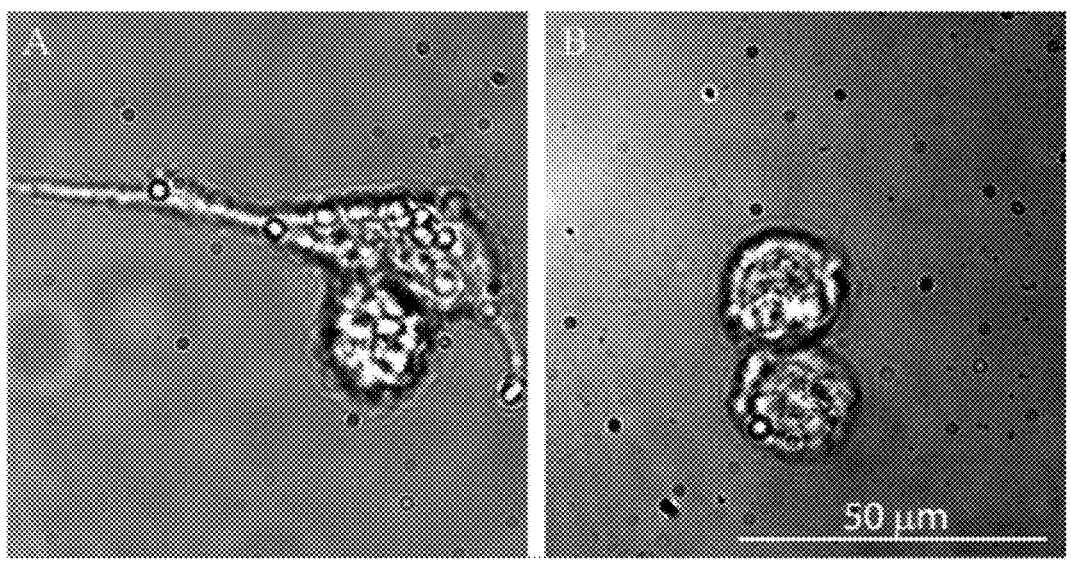
FIGS. 6A and 6B are images of the associated and entry of nanoparticles according to the present invention relative to: (A) control cells; and (B) fluorescently tagged nanoparticles showing that the nanoparticles were readily internalized by MH7A cells.

To confirm that the PSA-TMC nanoparticles could be internalized by cells in the absence of an active moiety that would facilitate receptor-mediated endocytotic uptake, the nanoparticles were surface modified with a near infrared fluorescent tag and uptake into the MH7A rheumatoid arthritis synovial fibroblast cell line was observed. As illustrated in FIG. 6, even after only a short incubation period, the nanoparticles were able to successfully associate with and enter the cells.

Materials for use in synthesizing and using the present invention are available from various vendors. For example, polysialic acid may be obtained from from Nacalai USA, Inc. (San Diego, Calif., USA). Chitosan (Mw 100K-300KDa) may be obtained from Acros Organics (Fair Lawn, N.J., USA). Sodium hydroxide (extra pure, pellets), tripolyphosphate (pure), acetonitrile (HPLC grade) may also be obtained from Acros Organics (New Jersey, USA). Sodium iodide (puriss), methyl iodide (reagent plus), 1-methyl-2-pyrrol idi none (anhydrous), ethanol (reagent alcohol), ammonomium acetate, deuterium oxide, and acetic acid (ACS reagent grade) may be obtained from Sigma (St. Louis, Mo., USA). Hydrochloric acid (ACS plus grade) may be provided by Fisher Scientific (Hanover Park, Ill., USA). Finally, methotrexate may be purchased from Enzo Life Science (Farmingdale, N.Y., USA). All chemical reagents may be used without further purification. A MH7A synovial fibroblast cell line was obtained from the Riken BRC through the National Bio-Resource Project of the MEXT, Japan. RPM I-1640, D-PBS, HEPES, L-glutamine, fetal bovine serum (FBS), and penicillin-streptomycin may be purchased from Lonza, Inc. (Allendale, N.J.).

Figure 7:
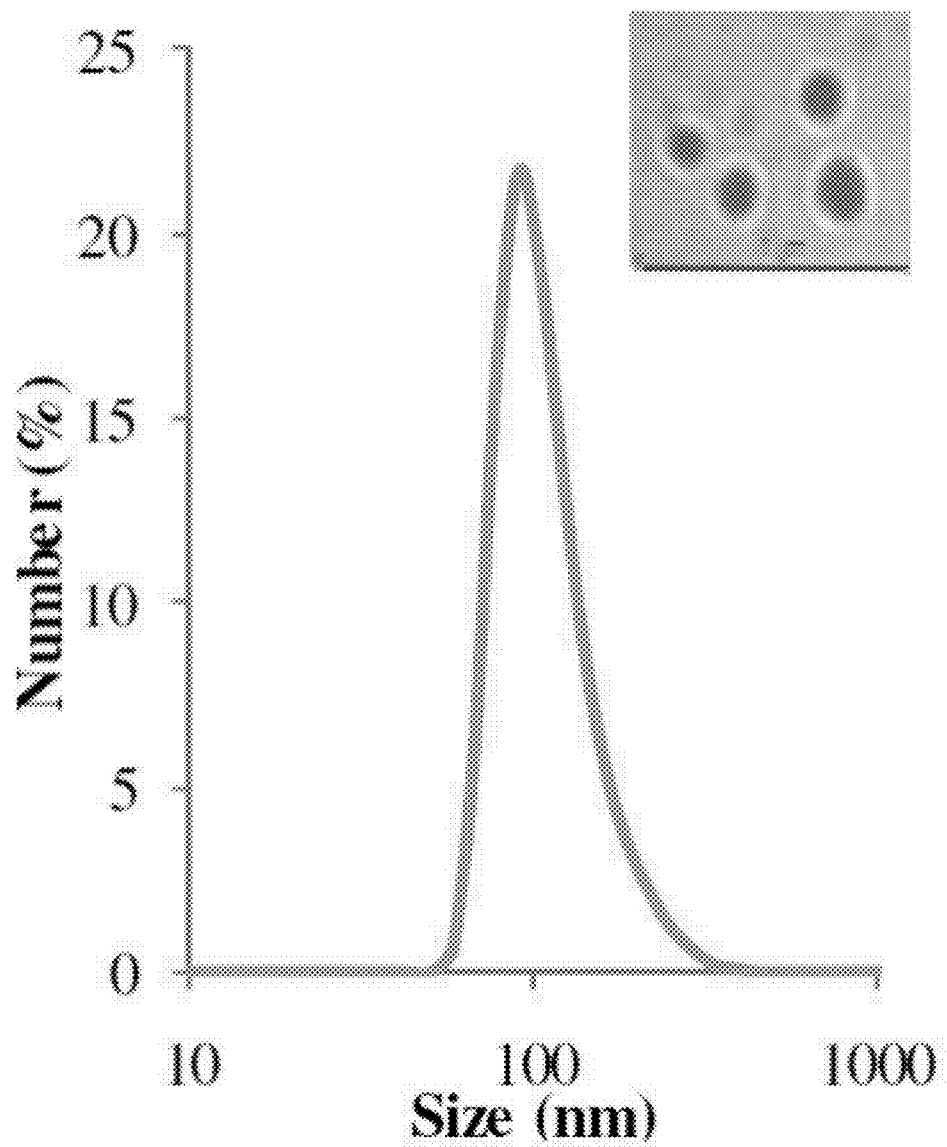
FIG. 7 is a graph of the size distribution of nanoparticles according to the present invention.
Figure 8:
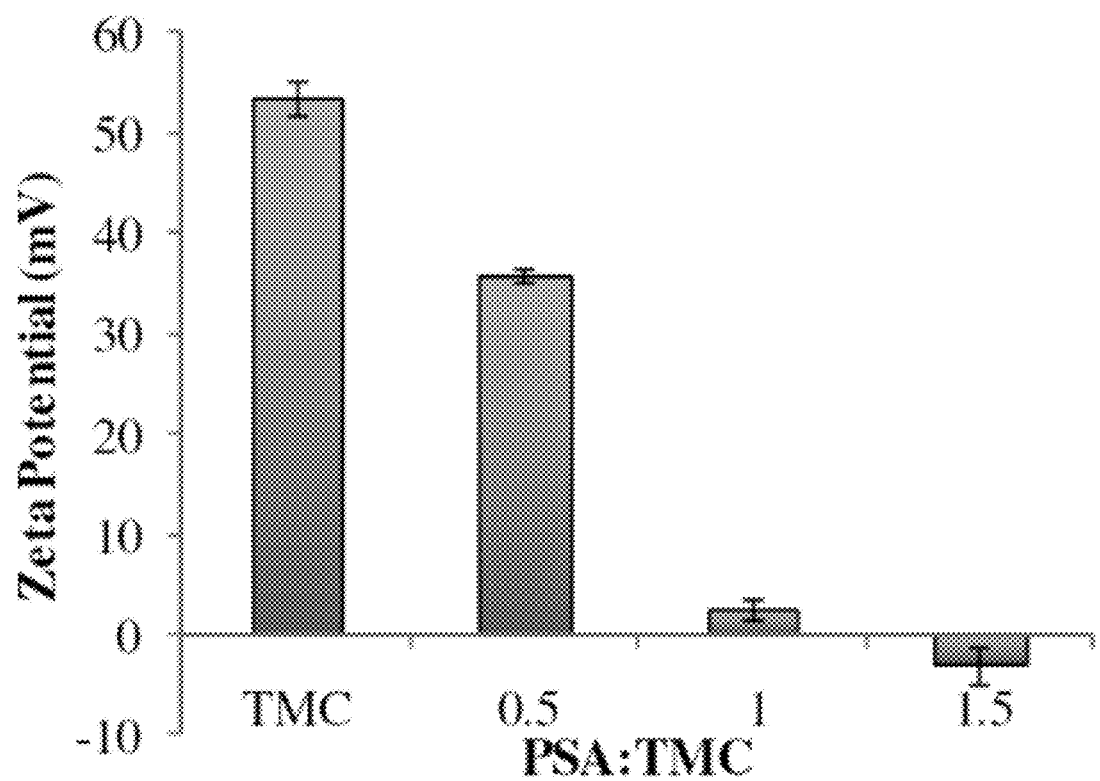
FIG. 8 is a graph of nanoparticle zeta potential as a function of PSA:TMC.
Figure 9:
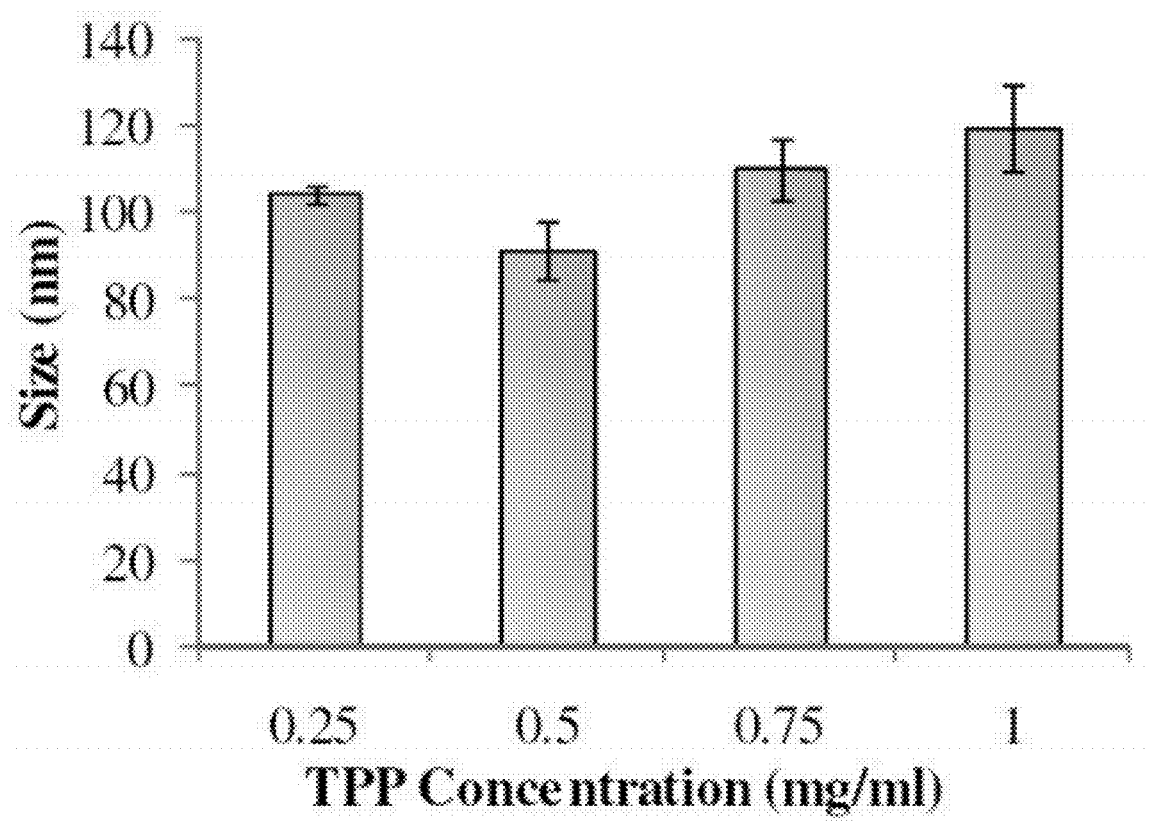
FIG. 9 is a graph of the size of nanoparticles according to the present invention based on TPP concentration.

Although TMC nanoparticles are known to suffer from large particle size and aggregation, an optimal ratio of 0.5 PSA:1 TMC was identified that resulted in nanoparticles with a small particle size of approximately 100 nm and a narrow distribution (PDI~0.125), as seen in FIG. 7. Other ratios yielded particles with large size and broad distribution, indicative of aggregation. As seen in FIG. 8, zeta potential measurements demonstrated that only PSA-TMC nanoparticles prepared at 0.5 PSA:1 TMC yielded a value of greater than 30 mV, consistent with discrete particle formation, as seen in FIG. 9. The size of the nanoparticles was not strongly dependent upon TPP concentration.

Figure 10:
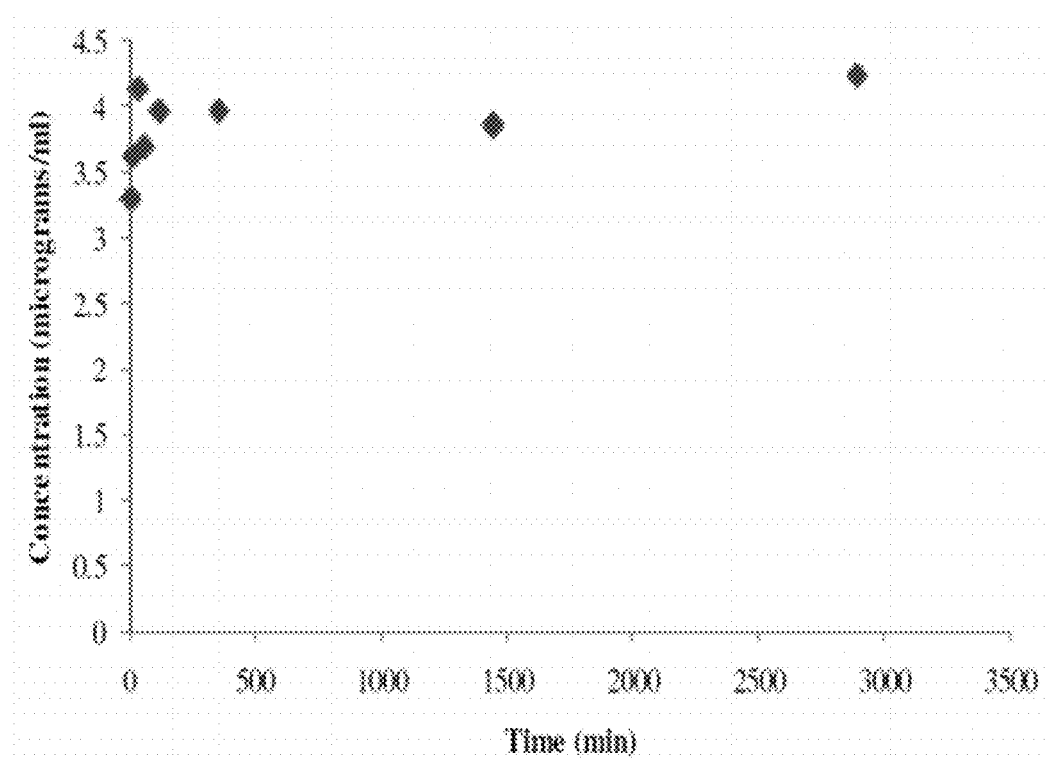
FIG. 10 is a graph of the controlled release of methotrexate from nanoparticles prepared with 10 wt. % MTX.
Figure 11:
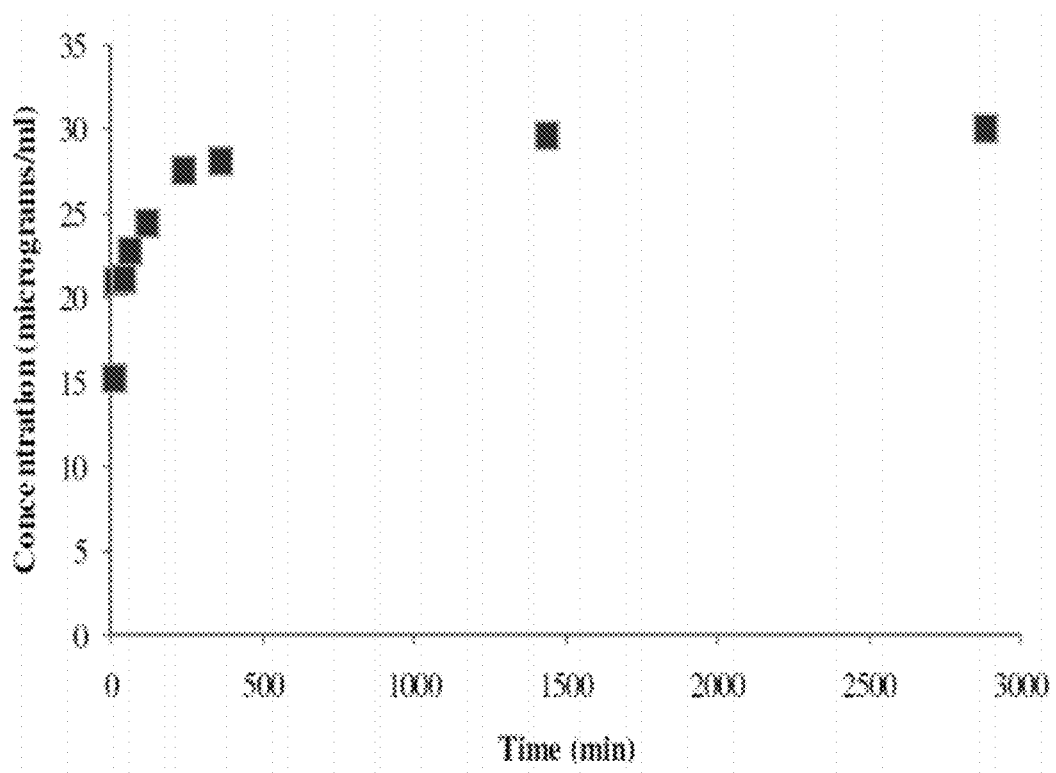
FIG. 11 is a graph of the controlled release of methotrexate from nanoparticles prepared with 25 wt. % MTX.

Referring to FIGS. 10 and 11, controlled release was demonstrated for nanoparticles prepared with both 10 and 25 wt. percent of MTX. Nanoparticles formulated with 25 wt. % of MTX yielded excellent encapsulation efficiency and loading capacity, as seen in Table 3 below:

TABLE 3

Loading capacity and encapsulation efficiency of PSA-based nanoparticles.

| Wt. % of Methotrexate | Loading Capacity (mg MTX/mg Nanoparticle) | Encapsulation Efficiency (%) |
|---|---|---|
| 10 | 0.025 | 15 |
| 25 | 0.088 | 40 |

These and other experiments demonstrating the efficacy of the preferred and alternative embodiments of the present invention were detailed in the appendices to U.S. Provisional Application No. 61/487,989, hereby incorporated by reference in its entirely. As explained above, the formation of nanoparticles having a ratio of PSA to TMC of 0.5:1 resulted in a delivery vehicle having optimal size, i.e., about 100 nm, and stability, i.e., over 30 mV zeta potential. It should be recognized by those of skill in the art that, although the preferred embodiment of the present invention provides for specific ratio of PSA to TMC, variations in the ratio of components used, as well as the other reaction materials, can impact both the size of the nanoparticles and their stability, as described above, and could be used to produce nanoparticles having a certain size and stability needed for a particular application.

What is claimed is:

1. A nanoparticle for delivering a pharmaceutical compound, comprising an ionic complex of polysialic acid and N-trimethyl chitosan, wherein said nanoparticle has a diameter of about 75 to about 125 nanometers.

2. The nanoparticle of claim 1, wherein said nanoparticle comprises polysialic acid and N-trimethyl chitosan in a ratio of 0.5 to 1 by weight.

3. The nanoparticle of claim 1, wherein said nanoparticle has a zeta potential above 30 millivolts.

4. The nanoparticle of claim 1, further comprising a pharmaceutical compound loaded in said nanoparticle.

5. The nanoparticle of claim 4, wherein said pharmaceutical compound is methotrexate.

6. The nanoparticle of claim 5, wherein said nanoparticle is loaded with about 10 percent by weight of said methotrexate relative to the weight of the nanoparticle.

\* \* \* \* \*